US011077217B2

(12) United States Patent
Li et al.

(10) Patent No.: US 11,077,217 B2
(45) Date of Patent: Aug. 3, 2021

(54) RADIOACTIVE LABELING METHOD FOR NEUROPEPTIDE Y DERIVATIVE COMPOUND AND MEDICINE FOR MULTI-TYPE BREAST CANCER THERAPY THEREOF

(71) Applicants: Ming-Hsin Li, Taoyuan (TW); Su-Jung Chen, Taoyuan (TW); Ming-Wei Chen, Taoyuan (TW); Yuan-Ruei Huang, Taoyuan (TW); Shih-Ying Lee, Taoyuan (TW); Chun-Fang Feng, Taoyuan (TW); Sheng-Nan Lo, Taoyuan (TW); Chih-Hsien Chang, Taoyuan (TW)

(72) Inventors: Ming-Hsin Li, Taoyuan (TW); Su-Jung Chen, Taoyuan (TW); Ming-Wei Chen, Taoyuan (TW); Yuan-Ruei Huang, Taoyuan (TW); Shih-Ying Lee, Taoyuan (TW); Chun-Fang Feng, Taoyuan (TW); Sheng-Nan Lo, Taoyuan (TW); Chih-Hsien Chang, Taoyuan (TW)

(73) Assignee: INSTITUTE OF NUCLEAR ENERGY RESEARCH, ATOMIC ENERGY COUNCIL, EXECUTIVE YUAN, Taoyuan (TW)

( * ) Notice: Subject to any disclaimer, the term of this patent is extended or adjusted under 35 U.S.C. 154(b) by 0 days.

(21) Appl. No.: 16/215,647

(22) Filed: Dec. 11, 2018

(65) Prior Publication Data

US 2020/0237938 A1 Jul. 30, 2020

(51) Int. Cl.
*A61K 51/08* (2006.01)
*A61K 51/04* (2006.01)
*A61K 51/06* (2006.01)

(52) U.S. Cl.
CPC ........ *A61K 51/088* (2013.01); *A61K 51/0482* (2013.01); *A61K 51/0497* (2013.01); *A61K 51/065* (2013.01)

(58) Field of Classification Search
CPC ...... A51K 51/00; A51K 51/08; A51K 51/088; A51K 51/0497; A51K 51/0482; A51K 2121/00; A51K 2123/00; A51K 51/04; A51K 51/06; A51K 51/065
USPC .... 424/1.11, 1.65, 1.69, 9.1, 9.2; 534/1, 1.1, 534/19.1, 19.2, 19.3, 19.4, 19.5, 19.6; 530/300
See application file for complete search history.

(56) References Cited

PUBLICATIONS

Ahren et al, Journal of Medicinal Chemistry, vol. 54, pp. 2368-2377 (Year: 2011).*
Li et al, Regenerative Biomaterials, pp. 215-219 (Year: 2015).*
Soloway et al, J. Med. Chem., vol. 10, No. 4, pp. 714-717 (Year: 1967).*

* cited by examiner

*Primary Examiner* — D. L. Jones (57) ABSTRACT

The present invention provides a radioactive labeling method for neuropeptide Y (NPY) compound and a mammalian diagnostic radioactive targeting medicine with NPY peptide being modified at position $27^{th}$ to $36^{th}$, and after binding with the chelating agent and labeling the radiation nucleus $^{66}$Ga、$^{67}$Ga、$^{68}$Ga、$^{177}$Lu or $^{111}$In to provide a radioactive targeting medicine for multi-type breast cancer diagnosis and treatment.

9 Claims, 5 Drawing Sheets

Specification includes a Sequence Listing.

RADIOACTIVE LABELING METHOD FOR NEUROPEPTIDE Y DERIVATIVE COMPOUND AND MEDICINE FOR MULTI-TYPE BREAST CANCER THERAPY THEREOF

BACKGROUND OF THE INVENTION

Incorporation-by Reference

1. A computer readable form sequence listing with file name "Original_MHL172_ST25.txt", 1040 bytes, created on 2020/03/23 is hereby submitted via EFS-Web.

Field of the Invention

The invention relates to a radioactive labeling medicine for breast cancer therapy, in particularly to a radioactive labeling for neuropeptide Y compound obtained with human neuropeptide Y as a main body being modified, binding with a chelating agent, and labeling with radioactive nucleus $^{66}$Ga、$^{67}$Ga、$^{68}$Ga、$^{177}$Lu and $^{111}$In to form a radioactive labeling neuropeptide Y compound as a medicine for breast cancer diagnosis and treatment and for Boron Neutron Capture Therapy (BNCT).

2. Description of Related Art

According to a health and life statistics, the top ten causes of death in 2015 were led by malignant tumors for 34 consecutive years, accounting for 28.6% of all deaths in Taiwan. Among them, the death rate of female breast cancer is ranked fourth in women's top ten cancer deaths and the highest incidence amid women's cancers, thus the development of effective diagnosis will be helpful to the breast cancer treatment to reduce the mortality rate of women's breast cancer in Taiwan.

Neuropeptide Y (NPY) consists of 36 amino acids forming peptides, which contain five subtype receptors are mainly divided into hY1, hY2, hY4, hY5 and hY6. NPY is a widely present in nervous system and regulate in vivo metabolism, such as obesity, stress, pain and blood pressure control.

According to Ruscica study 2007, NPY has been shown to be involved in the development of many cancers, including cell proliferation, angiogenesis and metastasis. In addition, research on breast cancer, many scholars use NPY for breast cancer treatment or diagnosis of related research with considerable success. Therefore, the development of neuropeptide (NPY) diagnostic medication will become a mainstream in the near future for treatment of malignant neoplasms. NPY plays its biological function through the five G-protein coupled receptors, named hY1, hY2-, hY4-, hY5- and hY6-R, associated with different aspects of the tumor. hY1R appears to be involved in the regulation of tumor cell proliferation, whereas hY2R promoter appears to promote neovascularization.

The development of NPY receptor subtype selective analogs helps to clarify the physiological and pathophysiological effects and the orientation of each receptor and may help to better understand receptor-ligand interactions. The NPY system appears to be varied with specific tumors to varying degrees, including spinal cord cell tumors, breast cancer and prostate cancer. NPY has also been shown to induce neuronal and smooth muscle cell proliferation and related to receptor hY1 expression; and hY1 expression and hY2R diffusion can induce spinal ridge tumors (Kitlinska et al. 2005), and the increased plasma NPY can be labeled for the formation of neuroblastoma.

The Y-receptor expression exists in human breast cancer, and it has shown that more than 90% of all breast tumors were associated with 100% of the examined metastatic expression of the hY1 receptor. It is worth noting that the metastatic subtype of the receptor has a potential correlation between the hY2 receptor in the healthy tissue and the hY1 receptor during tumor discovery. Studies (ChemMedChem 2015, 10, 164-172) have shown that the receptor hY1 is much larger than the EC2 expression of hY2 in the NPY derivative marker 3 boron neutrons in breast cancer cells. Literature (J Nucl Med May 1, 2016 vol. 57 no. Supplement 2 1076) disclosed that NPY derivatives labeled $^{64}$Cu (Pro30, Tyr32, Leu34, NPY (27-36) —NH$_2$), and Mengjie Liu (Int J Pept Res Ther (2013) 19: 33-41 DOI 0.1007/s10989-012-9330-z) disclosed that only 27-36 NPY sequences were selected for transformation and improved with hY1R junction, but tumor to muscle was not high.

According to a 2007 study by Ruscica, NPY has been shown to be involved in the development of many cancers (Regen Biomater. 2015 September; 2(3): 215-219), and studies on breast cancer have led to the discovery that NPY receptor hY1 is expressed in Breast cancer cells, metastatic subtypes of receptors from hY2 receptors to hY1 receptors in healthy tissues. During tumor discovery, more than 90% of all breast tumors and 100% of examined metastases express hY1 receptors, especially at the 27th to 36th amino acids in the sequence of the NPY are highly expressed in breast cancer hY1R.

Neuropeptide Y (NPY) and the hY1R-selective were selected for the NPY derivative of Re/99mTc-[Phe7, Pro34], which can visualize tumor sites and bone metastases in patients. However, the reaction was first carried out for 24 hours, and the chelate was changed to Nα-histidinyl acetyl (NαHis-ac) chelator, and the reaction was carried out at pH 3-4, and the yield was only 55%.

However, in order to apply boron-containing medicine BNCT, it is necessary to have a high degree of specificity for tumor cells. It is best to achieve a ratio of tumor concentration to normal tissue concentration (T/N) of more than 2.5 times. First, diagnosis with F-18 medicine, such as $^{18}$F-FBPA, to determine the tumor and normal tissue (TN) up to 2.5 times above that can be diagnosed and treated. During the BNCT treatment, patients need to continuously inject boron-containing medicines to maintain a tumor concentration and normal tissue concentration ratio (T/N) greater than 2.5 times, so that boron-containing medicines can be developed in the body for long time circulation.

The commonly used medicines for BNCT are BSH (Biodistribution of sodium borocaptate) or BPA (Boronophenylalanine). Therefore, the development of polymorphic breast cancer medicines for the treatment of neuropeptides and the selection of neuropeptides 27-36. The sequence is replanted, combined with boron-containing molecules and blood protein affinity molecules, which can be specifically and long-acting cycled, and can be combined with targeted diagnostic therapeutic functions and boron neutron treatment functions.

Prior arts WO 2007039318 A2 and US 20040076581 A1 revealed that Neuropeptide Y (NPY) and Y1R-selective with selection of Re/99mTc for labeling NPY derivatives-[Phe7, Pro34] to produce obvious images in the patient's tumor site and bone metastases. However, the NPY derivatives labeling needs to be modified with N$^\alpha$-histidinyl acetyl (N$^\alpha$His-ac) chelator and reacted at pH 3-4 for 24-hour and the yield was only 55%. In addition, the prior art Chinese Patent Publication No. CN104650217 A discloses the use of Evans Blue or Evans Blue derivative modified Exendin-4 for the treatment of Type II diabetes and myocardial infarction, although the same use of Evans Blue or Evans Blue modified compound in accordance with the present invention, however, the present invention provides a linker which can be combined with a chelating agent for labeling radioactive species $^{66}$Ga, $^{67}$Ga, $^{68}$Ga, $^{177}$Lu, $^{111}$In.

It is well known that the labeling process of $^{123}$I, $^{64}$Cu isotope is required to operate at the cyclotron site and the operation is complex, whereas the $^{61}$Ga and $^{111}$In labeling process are not required at the cyclotron site. The $^{111}$In labeling is advantageous to use in pharmacokinetics and pharmacological observation, and $^{177}$Lu with β-ray can be used in the diagnosis and treatment of tumors.

SUMMARY OF THE INVENTION

The primary object of the present invention is for the development of multi-type breast cancer diagnosis and treatment with neuropeptide Y derivatives, using PRRT (peptide receptor radionuclide treatment) and BNCT (boron neutron capture treatment), through the use of small fragment peptides and therapeutic radionuclides combination, combined with boron-containing molecules to develop a multi-type diagnosis and treatment of breast cancer medicines, the advantage is that increasing the accumulation of medicines in the tumor and the ratio of tumor to normal tissue (T/N) will be higher than the traditional BNCT medicines.

Another object of the present invention is to provide a neuropeptide Y derivative compound for multi-type breast cancer diagnosis and treatment, including (1) a metal chelating agent, such as DOTA, NOTA, or DTPA for performing a radioactive labeling with species ($^{66}$Ga, $^{67}$Ga, $^{68}$Ga, $^{177}$Lu, or $^{111}$In.). (2) protein affinity molecules in blood can be used to prolong medicine circulation time. (3) bonding substances, such as amino acids or polymers, prolonging the circulation time of the medicine in the body, (4) boron-containing compound, which can be used as boron neutron capture treatment, (5) the amino acid sequence of the human neuropeptide Y (NPY) derivative is selected at 27th-36th positions of the neuropeptide Y (NPY) having high affinity with breast cancer h1R. The neuropeptide Y derivative compound of the present invention can be developed and used as a companion diagnostics (CDx) and a therapeutic medicine using positron PET and single photon SPECT for multi-type breast cancers.

DETAILED DESCRIPTION OF THE PREFERRED EMBODIMENTS

The present invention aims to develop a multi-type breast cancer diagnosis and treatment medicine NPY, and can be applied to radioactive targeting diagnosis and treatment and boron neutron capture treatment (BNCT) for breast cancer patients. A design of Neuropeptide Y (NPY) compound for the medicine of multi-type breast cancer diagnosis and treatment is shown in Table 1.

Figure 2:
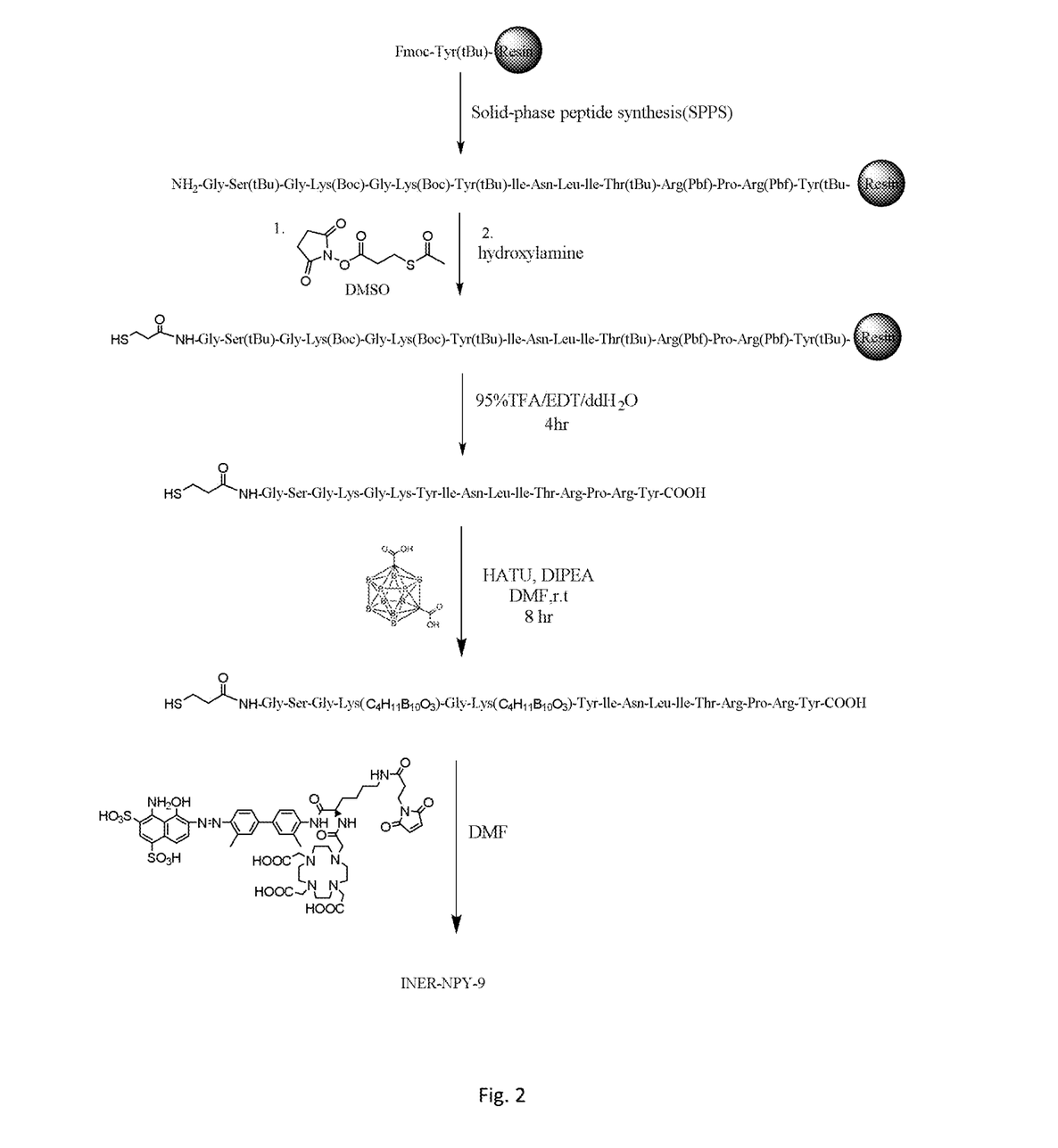
FIG. 2 is a flow chart of the synthesis of INER-NPY-9 of the present invention.

The present invention aims to develop a multi-type breast cancer diagnosis and treatment medicine NPY, and can be applied to radioactive targeting diagnosis and treatment and boron neutron capture treatment (BNCT) for breast cancer patients. The NPY derivative compound of the present invention comprising INER-NPY-1 to INER-NPY-10 as shown in Table 1, The neuropeptide Y (NPY) derivative compound, namely INER-NPY-9, is provided by the present invention for breast cancer radioactive and boron neutron capture therapy, and the flow chart of the synthesis of INER-NPY-9 is shown in FIG. 2. A schematic structure of the NPY derivative compound of the present invention is shown in Formula 1 below for description:

Formula 1 in which, R1 is a metal chelating agent for radioactive labeling $^{66}$Ga, $^{67}$Ga, $^{68}$Ga, $^{177}$Lu, or $^{111}$In; EB* is blood albumin affinity molecules for prolonging circulation time of the NPY derivative compound in vivo; each of R2 and R2' is a linker consisting of 1 to 10 amino acids or 4 to 10 polyethylene glycol (PEG) to enhance hydrophilicity and circulation time of the NPY derivative compound in vivo; B1 is a boron-containing molecule m-carborane-1, 7-dicarboxylic acid ($C_4H_{11}B_{10}O_3$) or maleimide-($S_{10}B_{12}H_{11}$) and is bonded at $NH_2$ side with amino acid including K (Lys), R(Arg), N(Asp), or Q (Glu) for boron neutron capture therapy; and the neuropeptide Y derivative includes amino acids at 27th to 36th positions in the sequence of neuropeptide Y, and the selected sequence is modified to YINLITR-PRY (SEQ ID NO. 3), which is modified at 34th amino acid of NPY The NPY derivative can also be selected at the 28th to 36th amino acid in the NPY sequence and the selected sequence is modified to YNLITRPRY (SEQ ID NO. 1), which is modified at 28th and 34th amino acid of NPY, or INLITRPRY (SEQ ID NO. 2), which is modified at 34th amino acid of NPY.

The structure of the NPY derivative compounds having each respective peptide sequence are shown in Table 1.

TABLE 1

| Code | Nomenclature | NPY Derivative Compound |
|---|---|---|
| 1 INER-NPY-1 | DOTA-GSG-YNLITRPPY (SEQ ID NO. 1) | DOTA-Gly-Ser-Gly -Tyr-Asn-Leu-Ile-Thr-Arg-Pro-Arg-Tyr (SEQ ID NO. 1) |
| 2 INER-NPY-2 | DOTA-GSG-INLITRPRY (SEQ ID NO. 2) | DOTA-Gly-Ser-Gly -Ile-Asn-Leu-Ile-Thr-Arg-Pro-Arg-Tyr (SEQ ID NO. 2) |
| 3 INER-NPY-3 | DOTA-PEG$_4$-YNLIRPRY (SEQ ID NO. 1) | DOTA-PEG$_4$-Tyr-Asn-Leu-Ile-Thr-Arg-Pro-Arg-Tyr (SEQ ID NO. 1) |
| 4 INER-NPY-4 | DOTA-PEG$_4$-INLITRPRY (SEQ ID NO. 2) | DOTA-PEG$_4$-Ile-Asn-Leu-Ile-Thr-Arg-Pro-Arg-Tyr (SEQ ID NO. 2) |
| 5 INER-NPY-5 | DOTA-GSG-K-YINLITRPRY (SEQ ID NO. 3) | DOTA-Gly-Ser-Gly-Lys-Tyr-Ile-Asn-Leu-Ile-Thr-Arg-Pro-Arg-Tyr (SEQ ID NO. 3) |
| 6 INER-NPY-6 | DOTA-GSG-K($C_4H_{11}B_{10}O_3$)-YINLITRPRY (SEQ ID NO. 3) | DOTA-Gly-Ser-Gly-Lys-($C_4H_{11}B_{10}O_3$)-Tyr-Ile-Asn-Leu-Ile-Thr-Arg-Pro-Arg-Tyr (SEQ ID NO. 3) |
| 7 INER-NPY-7 | DOTA-GSG-KGK-YINLITRPRY (SEQ ID NO. 3) | DOTA-Gly-Ser-Gly-Lys-Tyr-Ile-Asn-Leu-Ile-Thr-Arg-Pro-Arg-Tyr (SEQ ID NO. 3) |
| 8 INER-NPY-8 | DOTA-GSG-K($C_4H_{11}B_{10}O_3$)-GK($C_4H_{11}B_{10}O_3$-YINLITRPRY (SEQ ID NO. 2) | DOTA-Gly-Ser-Gly -Lys($C_4H_{11}B_{10}O_3$)-Gly-Lys-($C_4H_{11}B_{10}O_3$)-Tyr-Ile-Asn-Leu-Ile-Thr-Arg-Pro-Arg-Tyr (SEQ ID NO. 2) |
| 9 INER-NP7-9 | DOTA-EB*-GSG-K($C_4H_{11}B_{10}O_3$)-GK($C_4H_{11}B_{10}O_3$)-YINLITRPRY (SEQ ID NO. 3) | DOTA-EB*-Gly-Ser-Gly-Lys-($C_4H_{11}B_{10}O_3$)-Gly-Lys-($C_4H_{11}B_{10}O_3$)-Tyr-Ile-Asn-Leu-Ile-Thr-Arg-Pro-Arg-Tyr (SEQ ID NO. 3) |
| 10 INER-NPY-10 | DOTA-EB*-GSG-K(malemide-$S_{10}B_{12}H_{11}$)-GK(malemide-$S_{10}B_{12}H_{11}$)-YINLITRPRY (SEQ ID NO. 3) | DOTA-EB*-Gly-Ser-Glly-Lys-(maleimide-$S_{10}B_{12}H_{11}$)-Gly-Lys-(maleimide-$S_{10}B_{12}H_{11}$)-Tyr-Ile-Asn-Leu-Ile-Thr-Arg-Pro-Arg-Tyr (SEQ ID NO. 3) |

In the Table 1, the peptide sequences are shown in Formula 2a, 2b, and 2c below with respective schematic structure.

1) NPY derivative having peptide in sequence YNLITR-PRY (SEQ ID NO. 1): Tyr-Asn-Leu-Ile-Thr-Arg-Pro-Arg-Tyr (SEQ ID NO. 1) is shown in Formula 2a:

Formula 2a

2) NPY derivative having peptide in sequence INLITR-PRY (SEQ ID NO. 2): Ile-Asn-Leu-Ile-Thr-Arg-Pro-Arg-Tyr (SEQ ID NO. 2) is shown in Formula 2b:

Formula 2b

3) NPY derivative having peptide in sequence YINLITR-PRY (SEQ ID NO. 3): Tyr-Ile-Asn-Leu-Ile-Thr-Arg-Pro-Arg-Tyr (SEQ ID NO. 3) is shown in Formula 2c:

Formula 2c

Embodiment 1: The Synthesis of the Blood Albumin Affinity Molecule

Figure 1:
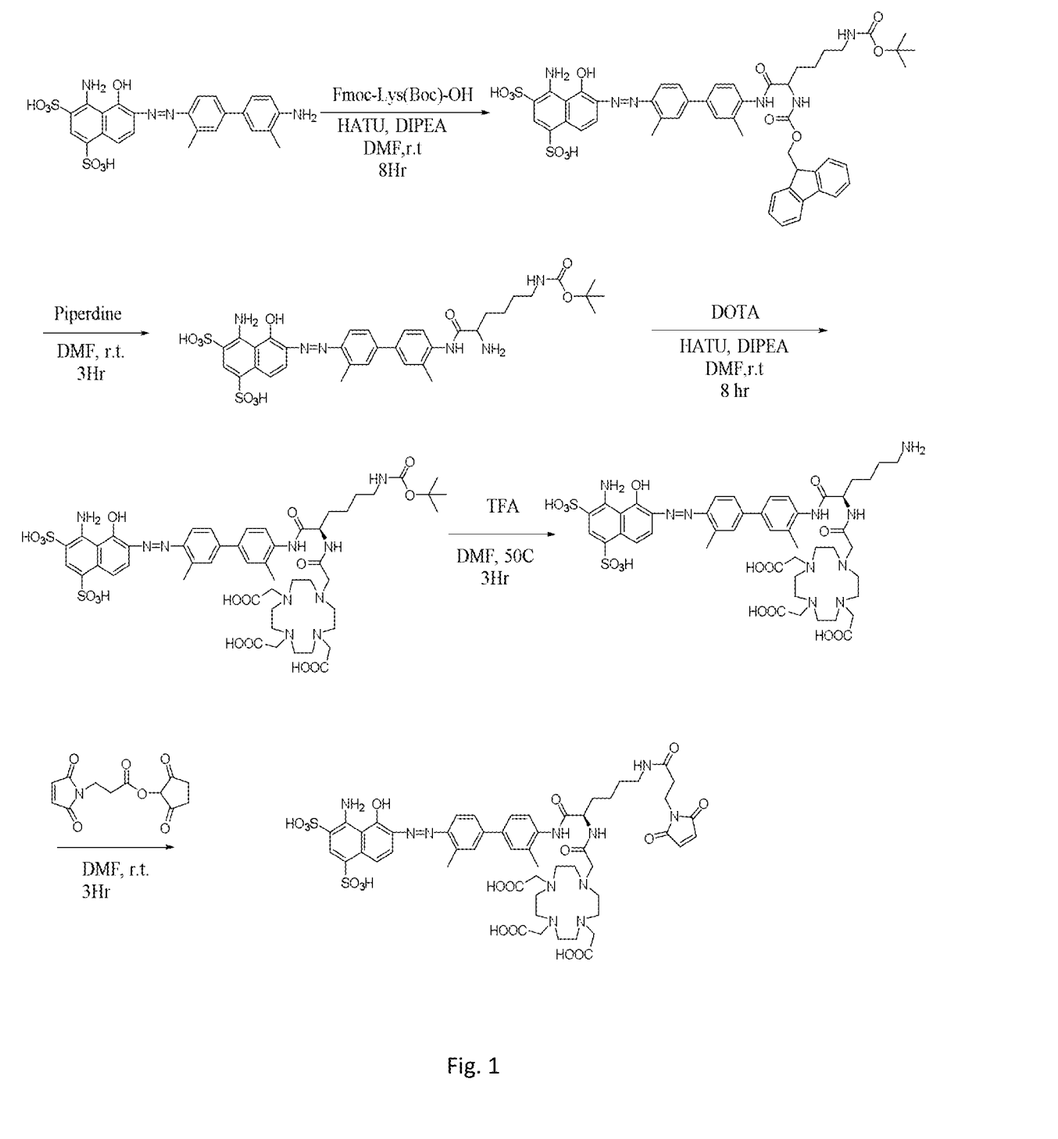
FIG. 1 is a synthesis of the blood albumin affinity molecule.

The synthesis of the blood albumin affinity molecule is shown in FIG. 1, comprising steps: dissolving EB-NH$_2$ and Fmoc-Lys(Boc)-OH in DMF solvent, and HATU and DIPEA are added and reacted at room temperature for 8 hours to form EB-Fmoc-Lys(Boc):

adding EB-Fmoc-Lys (Boc) to Pipedine and DMF, and reacted at room temperature for 3 hours to form EB-Lys (Boc);

dissolving EB-Lys (Boc) in DMF solvent, and DOTA chelating group, HATU, and DIPEA were added, and reacting at room temperature for 8 hours to form DOTA-EB-Fmoc-Lys (Boc); adding TFA and DMF to DOTA-EB-Fmoc-Lys(Boc) to form DOTA-EB-Fmoc-Lys; and adding DOTA-EB-Fmoc-Lys to the Maleimide derivative and reacting at room temperature for 3 hours to form an Evans Blue-lysine derivative.

Embodiment 2: The Synthesis of INER-NPY-9 of the Present Invention

The synthesis of INER-NPY-9 of the present invention is shown in FIG. 2, comprising steps: synthesizing Fmoc-Tyr (tBu)-wang resin and neuropeptide amino acid by solid phase peptide synthesis (SPPS)

removing the protecting group and the resin with 95% TFA/EDT/ddH$_2$O lysate after the N-terminal NH$_2$ is vulcanized to sulfide;

adding HATU, DIPEA, and DMF to react at room temperature for 8 hours, and bonding the NH$_2$ at lysine side with $C_4H_{11}B_{10}O_3$; and reacting of DOTA-EB-lysine in DMF solvent for 12 hours at room temperature to obtain the INER-NPY-9 peptide.

Figure 3:
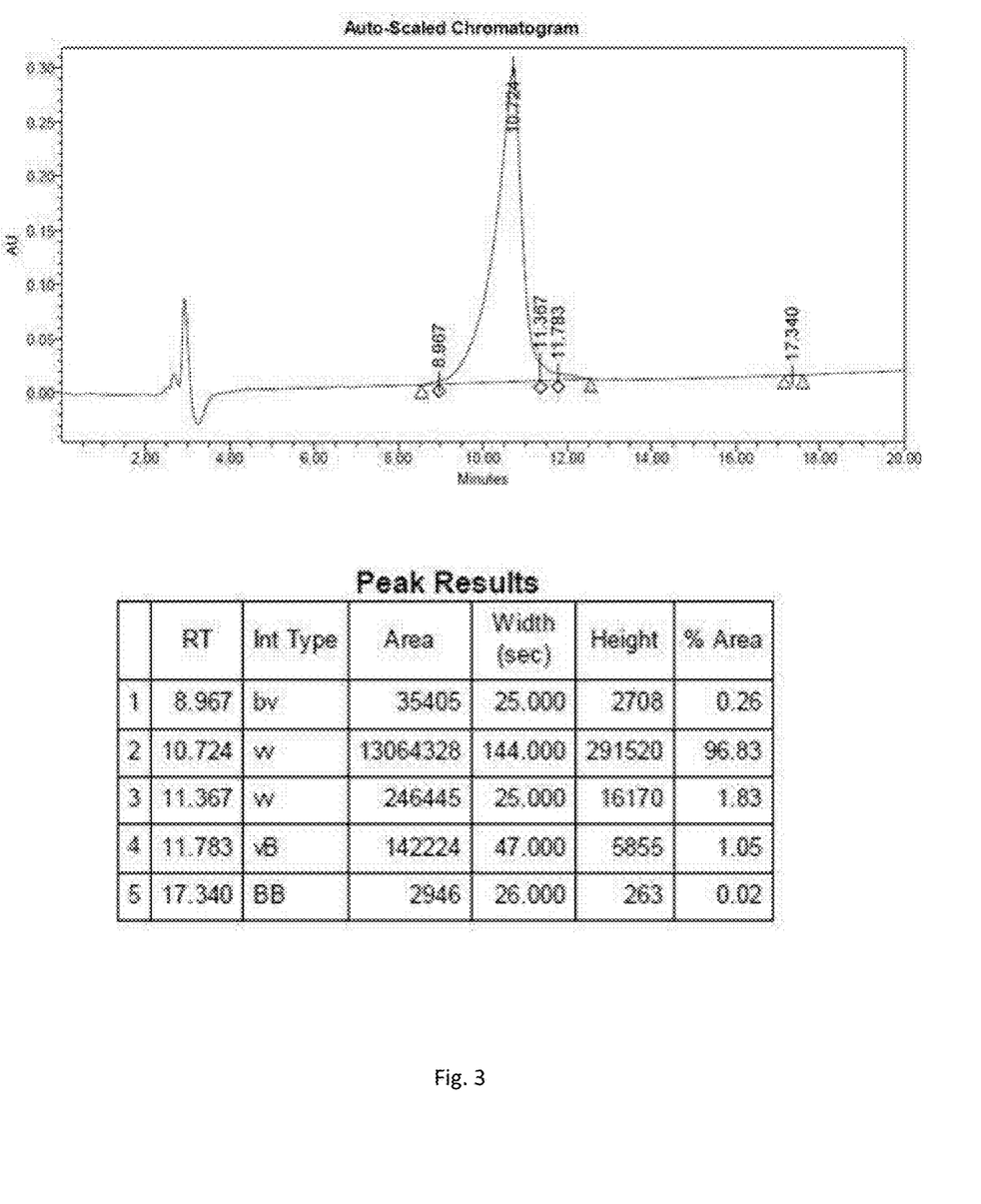
FIG. 3 is a experimental result showing labeling of neuropeptide Y derivative compound of the present invention.

Embodiment 3: Experimental Result of Labeling NPY Derivative Compound and the Radiochemical Purity Analysis by Radio-HPLC The experimental result of labeling NPY derivative compound is shown in FIG. 3, comprising steps:

providing 30 μg of one of from INER-NPY-1 to INER-NPY-9 peptide, and dissolving and mixing in 30 μL DMSO;

adding 0.2M NaOAc buffer and a radioactive isotope from one of $^{111}$In, $^{68}$Ga, $^{177}$Lu having activity from 3 to 12 mCi, a total reaction volume 300 μL, and pH of the solution from 5 to 6, to the solution;

reacting the solution in a range from 85 to 100° C., preferably 95° C., for 10 to 30 minutes, preferably 15 minutes;

taking 1 μL of the solution after cooling for efficiency analysis by Radio-TLC (using TLC (1*10 cm) ITLC-SG strip, and the developing solution is 0.1 M and Citric acid:Sodium Citrate=2:8 (V:V); taking the solution 20~30 μCi and carrying out Radio-HPLC radiochemical purity analysis (waters HPLC system with radiation detector for radio-chemical purity analysis, Column: Aglient, ZORBAX SB-C18, 5 μm, 80 Å, 4.6×250 mm, flow rate: 0.8 mL/min, analysis wavelength: 220 nm, mobile phase A: 20% ACN+0.1% TFA, mobile phase B: 80% water+0.1% TFA).

The radiochemical purity analysis results of In-111-INER-NPY-9 by Radio-HPLC are shown in FIG. 3, in which the main signal has a residence time of about 11 minutes.

Figure 4A:
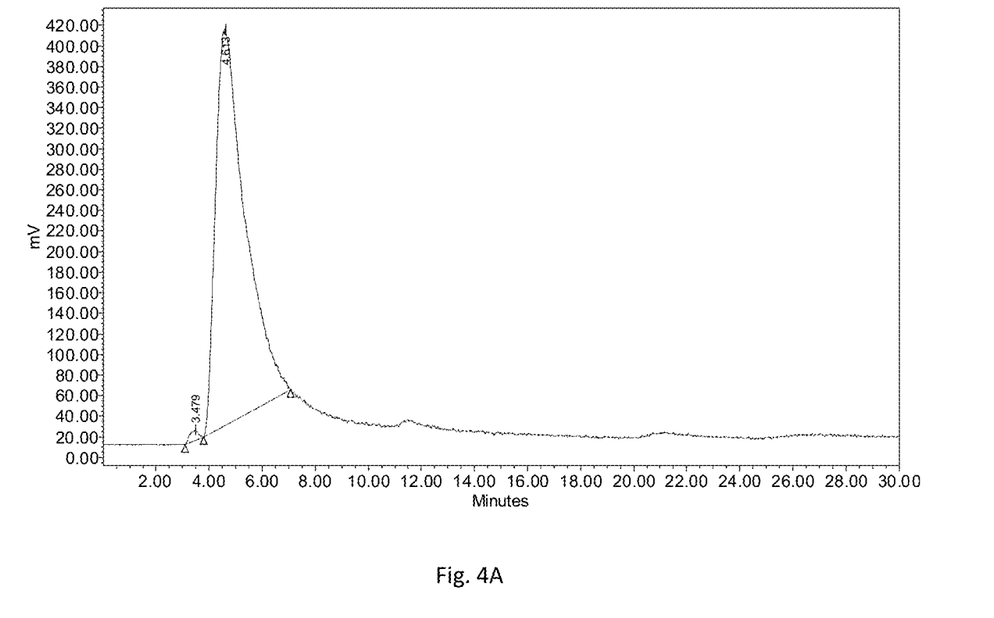
FIG. 4A is a RP-HPLC analysis spectrum of free $^{111}$In-INER-NPY-9.
Figure 4B:
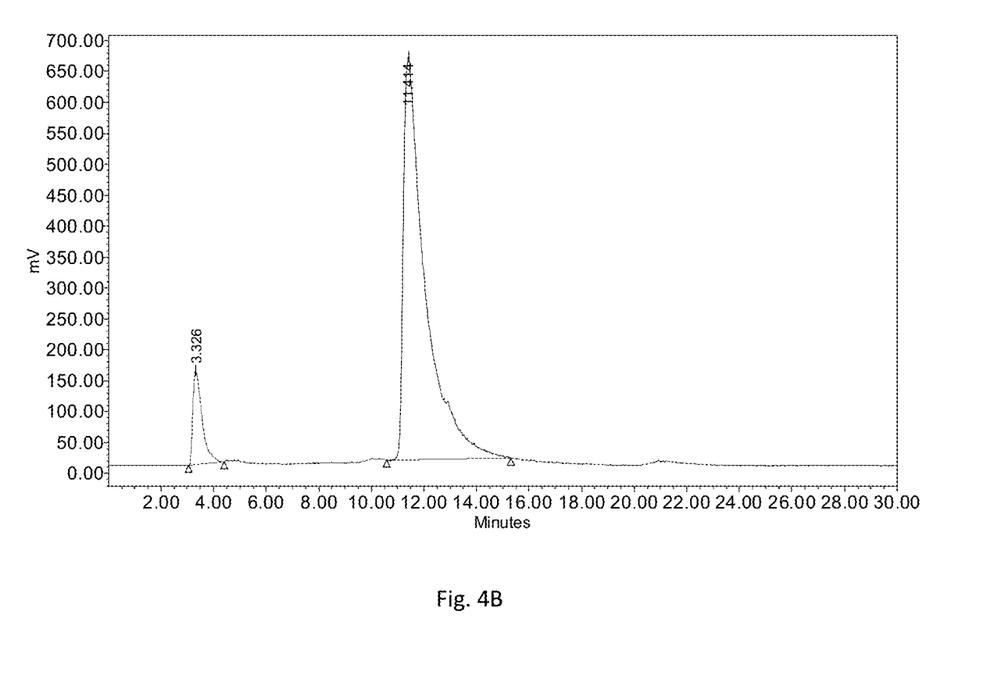
FIG. 4B is a RP-HPLC analysis spectrum of $^{111}$In-INER-NPY-9.

The RP-HPLC analysis spectrum of free-$^{111}$In INER-NPY-9 and $^{111}$In-INER-NPY-9 are shown in FIG. 4A and FIG. 4B, respectively.

Figure 5:
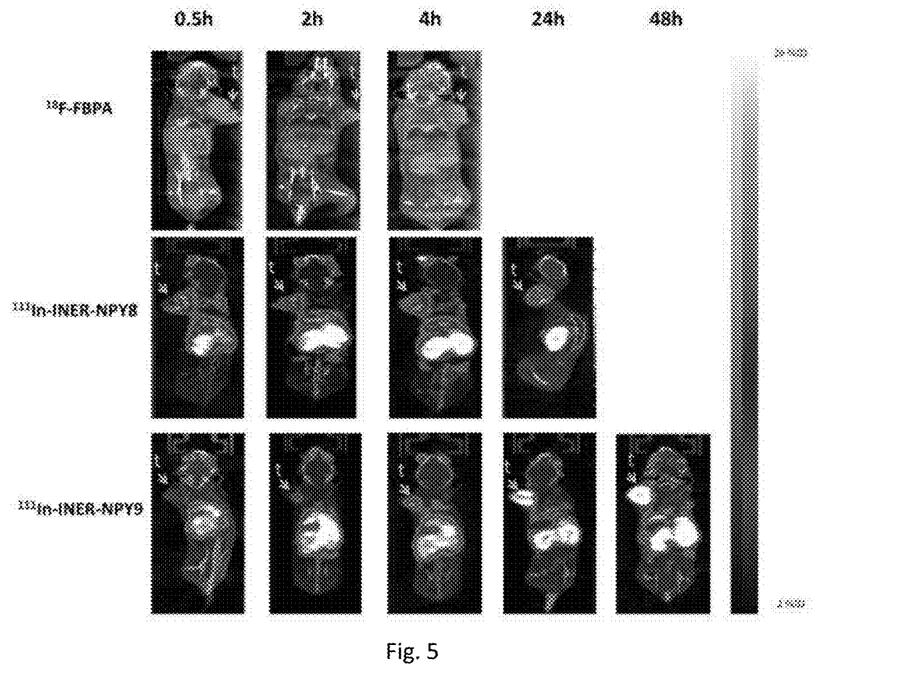
FIG. 5 is a 4T1 tumor animal model angiogram with alphabet "t" indicating tumor.
Figure 6:
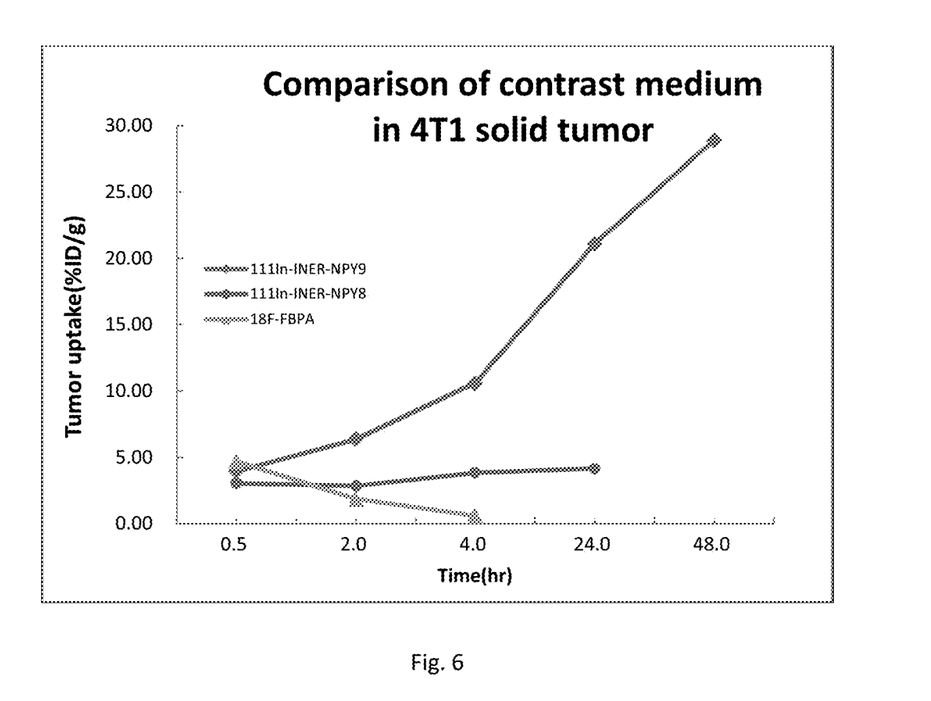
FIG. 6 is a comparison of tumor absorption rate between medicines of commercial $^{18}$F-FBPA and the $^{111}$In-INER-NPY-9 of the present invention.

Embodiment 4: Radioactive Labeling Neuropeptide Y Derivative in 4T1 Tumor Animal Model with Radio-HPLC for Analyzing the Labeling Purity In animal studies, tumor xenografts were performed in 6-week-old female BALB/c mice by subcutaneous injection of 2×10$^6$ 4T1 cells, and $^{111}$In-INER-NPY8 and $^{111}$In-INER-NPY9 were injected into the tail vein, and Nano-SPECT/CT imaging was performed at 0.5, 2, 4, 24, and 48 hours, respectively, and compared with $^{18}$F-FBPA for PET contrast images. The results are shown in FIG. 5 and FIG. 6, respectively.

We claim:

1. A neuropeptide Y (NPY) derivative compound of Formula 1,

[Formula 1 structure showing: R1—EB*—R2—NH—CH(—CH2CH2CH2CH2—HN—B1)—C(=O)— and —R2'—NH—CH(—CH2CH2CH2CH2—HN—B1)—C(=O)—NPY derivative]

wherein R1 is a metal chelating agent;
EB* is Evans Blue or Evans Blue-lysine;
R2 is a first linker selected from the group consisting of 1 to 10 amino acids and 4 to 10 polyethylene glycol (PEG);
R2' is a second linker selected from the group consisting of 1 to 10 amino acids and 4 to 10 polyethylene glycol (PEG);
B1 is $C_4H_{11}B_{10}O_3$ or $S_{10}B_{12}H_{11}$; and
NPY derivative is selected from the group consisting of SEQ ID NO. 1, SEQ ID NO. 2, and SEO ID NO. 3.

2. The neuropeptide Y (NPY) derivative compound of claim 1, wherein the metal chelating agent R1 is DOTA, NOTA, or DTPA.

3. The neuropeptide Y (NPY) derivative compound of claim 1, wherein the boron-containing molecule B1 at NH2 side is bonded with an amino acid K (Lys).

4. The neuropeptide Y (NPY) derivative compound of claim 1, wherein EB* is Evans Blue-lysine-.

5. The neuropeptide Y (NPY) derivative compound of claim 1, wherein NPY derivative is SEQ ID NO. 1 or SEQ ID NO. 2.

6. The neuropeptide Y (NPY) derivative compound of claim 1, wherein the NPY derivative is SEQ ID NO. 3.

7. The neuropeptide Y (NPY) derivative compound of claim 1, wherein the NPY derivative compound is DOTA-EB*-GSG-K($C_4H_{11}B_{10}O_3$)-GK($C_4H_{11}B_{10}O_3$) SEQ ID NO. 3 or DOTA-EB*-GSG-K($S_{10}B_{12}H_{11}$)-GK($S_{10}B_{12}H_{11}$) SEQ ID NO. 3.

8. A method of for radioactive labeling of the neuropeptide Y (NPY) derivative compound of claim 1, 2, 3, 4, 5, 6 or 7, comprising:
dissolving an amount of the NPY derivative compound in solution;
mixing said NPY derivative compound solution with a radioactive isotope selected from the group consisting of $^{111}$In, $^{68}$Ga and $^{177}$Lu;
wherein said NPY derivative compound is labeled with said radioactive isotope.

9. The method of claim 8, wherein the amount of NPY derivative compound is from 30μ to 100 μg.

* * * * *

SEQUENCE LISTING

<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: Synthetic Peptides

<400> SEQUENCE: 1

Tyr Asn Leu Ile Thr Arg Pro Arg Tyr
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide

<400> SEQUENCE: 2

Ile Asn Leu Ile Thr Arg Pro Arg Tyr
1               5

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

Tyr Ile Asn Leu Ile Thr Arg Pro Arg Tyr
1               5                   10